US011497465B2

(12) United States Patent
Sampath Kumaran

(10) Patent No.: US 11,497,465 B2
(45) Date of Patent: Nov. 15, 2022

(54) METHOD FOR TREATMENT OF A VASCULAR LESION

(71) Applicant: Bard Peripheral Vascular, Inc., Tempe, AZ (US)

(72) Inventor: Ranjani Sampath Kumaran, Tempe, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 422 days.

(21) Appl. No.: 16/663,530

(22) Filed: Oct. 25, 2019

(65) Prior Publication Data

US 2021/0121154 A1  Apr. 29, 2021

(51) Int. Cl.
*A61B 8/08* (2006.01)
*G06T 7/00* (2017.01)

(52) U.S. Cl.
CPC ............ *A61B 8/085* (2013.01); *G06T 7/0012* (2013.01); *G06T 2207/10132* (2013.01); *G06T 2207/30096* (2013.01); *G06T 2207/30101* (2013.01)

(58) Field of Classification Search
CPC ....... A61B 8/085; A61B 8/0891; A61B 8/481; A61B 8/52; A61B 8/5215; A61B 8/5223; A61N 7/00; A61N 7/02; A61N 7/022; A61N 2007/0073; A61N 2007/0043
See application file for complete search history.

(56) References Cited

U.S. PATENT DOCUMENTS

| 6,443,894 B1 | 9/2002 | Sumanaweera et al. |
| 7,744,537 B2 | 6/2010 | Kanai et al. |
| 8,075,488 B2 | 12/2011 | Burton |
| 8,187,188 B2 | 5/2012 | Yokota et al. |
| 8,313,437 B1 | 11/2012 | Suri |
| 8,708,914 B2 | 4/2014 | Suri |
| 8,718,344 B2 | 5/2014 | Kobayashi et al. |
| 8,885,905 B2 | 11/2014 | Dey et al. |
| 9,049,783 B2 | 6/2015 | Feofilovic |
| 9,061,131 B2 | 6/2015 | Jahnke et al. |
| 9,144,415 B2 | 9/2015 | Sata et al. |

(Continued)

OTHER PUBLICATIONS

Cryotherapy, my.clevelandclinic.org/health/treatments/21099-cryotherapy, retrieved Feb. 8, 2022.*

(Continued)

*Primary Examiner* — Carolyn A Pehlke
(74) *Attorney, Agent, or Firm* — Dinsmore & Shohl LLP

(57) ABSTRACT

A method for treatment of a vascular lesion. A biomarker insertion device introduces a biomarker into a vascular region. The biomarker binds to a lesion type of a plurality of lesion types. Under ultrasound imaging, an image brightness of an imaged biomarker differs based on the lesion type of the plurality of lesion types to which the biomarker binds. An ultrasound imaging probe of an ultrasound imaging system images the biomarker and produces an image brightness of the imaged biomarker. The lesion type is determined based on the image brightness of the imaged biomarker. A frequency of a high intensity focused ultrasound emission of a non-invasive high intensity focused ultrasound device is tuned based on the determined lesion type. The tuned frequency is applied to the vascular lesion, resulting in the destruction of the vascular lesion.

16 Claims, 3 Drawing Sheets

(56) References Cited

U.S. PATENT DOCUMENTS

| | | | |
|---|---|---|---|
| 9,232,932 B2 | 1/2016 | Kim et al. | |
| 9,398,857 B2 | 7/2016 | Choi et al. | |
| 9,526,923 B2 | 12/2016 | Jahnke et al. | |
| 9,538,988 B2 | 1/2017 | Miyachi | |
| 9,901,753 B2 | 2/2018 | Cain et al. | |
| 9,943,708 B2 | 4/2018 | Roberts et al. | |
| 9,955,946 B2 | 5/2018 | Miller et al. | |
| 10,293,187 B2 | 5/2019 | Cannata et al. | |
| 2006/0079868 A1* | 4/2006 | Makin | A61N 7/02 606/27 |
| 2010/0010393 A1 | 1/2010 | Duffy et al. | |
| 2010/0160781 A1 | 6/2010 | Carter et al. | |
| 2011/0098563 A1 | 4/2011 | Osaka | |
| 2011/0257527 A1 | 10/2011 | Suri | |
| 2012/0283564 A1* | 11/2012 | Ebbini | A61B 8/085 600/443 |
| 2014/0100440 A1 | 4/2014 | Cheline et al. | |
| 2015/0173716 A1 | 6/2015 | Lee | |
| 2015/0352379 A1* | 12/2015 | Appelman | A61N 7/02 606/27 |
| 2016/0310101 A1 | 10/2016 | Lee | |
| 2017/0049419 A1 | 2/2017 | Park et al. | |
| 2017/0215838 A1 | 8/2017 | Park et al. | |
| 2019/0125307 A1* | 5/2019 | Unger | A61B 5/0082 |

OTHER PUBLICATIONS

Norton, Cathy A. A Compilation of Geometric Distance and Tissue Property Data for the Human Thorax. Naval Undersea Warfare Center Newport Div Ri, 1995.*

Ross, Ryan D., and Ryan K. Roeder. "Binding affinity of surface functionalized gold nanoparticles to hydroxyapatite." Journal of biomedical materials research Part A 99.1 (2011): 58-66.*

Ergün, A. Sanh. "Analytical and numerical calculations of optimum design frequency for focused ultrasound therapy and acoustic radiation force." Ultrasonics 51.7 (2011): 786-794.*

Hamilton, Andrew J., et al. "Intravascular ultrasound molecular imaging of atheroma components in vivo." Journal of the American College of Cardiology 43.3 (2004): 453-460.*

Mayeux R. Biomarkers: potential uses and limitations. NeuroRx. 2004;1(2):182-188. doi:10.1602/neurorx.1.2.182.*

Damianou, Christakis, Removing atherosclerotic plaque created using high cholesterol diet in rabbit using ultrasound. Journal of Therapeutic Ultrasound, Jan. 29, 2015, Limassol, Cypress; https://www.ncbi.nlm.nih.gov/pmc/articles/PMC4314792.

Dogra, Vikram, High-intensity focused ultrasound use widens in research, practice, Apr. 1, 2007; https://www.diagnosticimaging.com/articles/high-intensity-focused-ultrasound-use-widens-research-practice.

Alpinion Medical Systems: HIFU Technology, Gyeonggi-do, Korea; from www.alpinion.com/web/technology/hifu.asp.

Yoshizawa, S. et al., High Intensity Focus Ultrasound Lithotripsy With Cavitating Microbubbles, Med Biol Eng Comput, Aug. 2009;47(8):851-60, Sendai, Japan; https://www.ncbi.nlm.nih.gov/pubmed/19360448.

Ikeda, Teiichiro, et al., Cloud Cavitation Control for Lithotripsy Using High Intensity Focused Ultrasound, Ultrasound in Medicine & Biology, vol. 32, Issue 9, Sep. 2006, pp. 1383-1397; https://www.sciencedirect.com/science/article/abs/pii/S0301562906016231.

Koizumi, Norihiro, et al., A Control Framework for the Non-Invasive Ultrasound Theragnostic System, The 2009 IEEE/RSJ International Conference on Intelligent Robots and Systems, Oct. 11-15, 2009 St. Louis, USA.

* cited by examiner

METHOD FOR TREATMENT OF A VASCULAR LESION

CROSS-REFERENCE TO RELATED APPLICATIONS

None.

TECHNICAL FIELD

The present invention relates generally to treatment of vascular lesions, and, more particularly, to a method of treatment of vascular lesions based at least in part on the lesion type.

BACKGROUND ART

Laser ablation, microwave coagulation, and radiofrequency ablation may be used in treating benign and malignant tumors, hemostasis, uterine fibroids, and other conditions. However, these treatments are invasive and/or ionizing, creating long-term effects. Moreover, these treatments may not be repeated as many times as required to fully destroy the targeted cells.

It is known to use High Intensity Focused Ultrasound (HIFU) lithotripsy in kidney stone applications, cellulite treatment, and tumor therapy. The difficulty in applying HIFU to lesion or plaque removal in a blood vessel is that the content of the lesion or plaque is not known, e.g., the lesion may be fatty, calcified, or fibrous, or a combination thereof.

In addition, there have been debates on the pathological effects or side effects of HIFU on tissues, since HIFU is a thermal modality.

What is needed in the art is an improved method for treatment of vascular lesions, particularly when the lesions are in the elastocalcinosis disease state.

SUMMARY OF INVENTION

The present invention provides a method for treatment of vascular lesions, such as when the lesions are in the elastocalcinosis disease state.

The invention in one form is directed to a method for treatment of a vascular lesion, including: introducing a biomarker into a vascular region, wherein the biomarker binds to a lesion type of a plurality of lesion types, wherein under ultrasound imaging, an image brightness of an imaged biomarker differs based on the lesion type of the plurality of lesion types to which the biomarker binds; imaging the biomarker under ultrasound imaging to determine the lesion type based on the image brightness of the imaged biomarker; determining the lesion type based on the image brightness of the imaged biomarker, thereby producing a determined lesion type; tuning a frequency of a high intensity focused ultrasound emission of a non-invasive high intensity focused ultrasound device based on the determined lesion type, wherein as a result of the tuning of the frequency of the high intensity focused ultrasound emission is a tuned frequency; and applying the high intensity focused ultrasound emission of the non-invasive high intensity focused ultrasound device to the vascular lesion at the tuned frequency to break up the vascular lesion.

An advantage of the present invention is an improved method of accurately identifying the contours of vascular lesion through the use of a diagnostic, biomarker-based, ultrasound imaging system.

Another advantage is the ability to produce a determined lesion type of the lesion based on the image brightness of the imaged biomarker, in order to tune a frequency of a HIFU emission of a HIFU probe of a non-invasive HIFU system based on the determined lesion type, and applying the tuned frequency of a HIFU emission of a non-invasive HIFU device to the vascular lesion at the tuned frequency in order to destroy, disintegrate, or otherwise ablate the vascular lesion.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIGS. 3 and 4 depict a system for treating a vascular lesion having multiple lesion types, wherein FIG. 3 is a schematic representation of an ultrasound imaging system and the lesion having multiple lesion types to which respective biomarkers bind, and FIG. 4 is a schematic representation of a non-invasive high intensity focused ultrasound system that applies a respective tuned frequency to each of the multiple lesion types.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
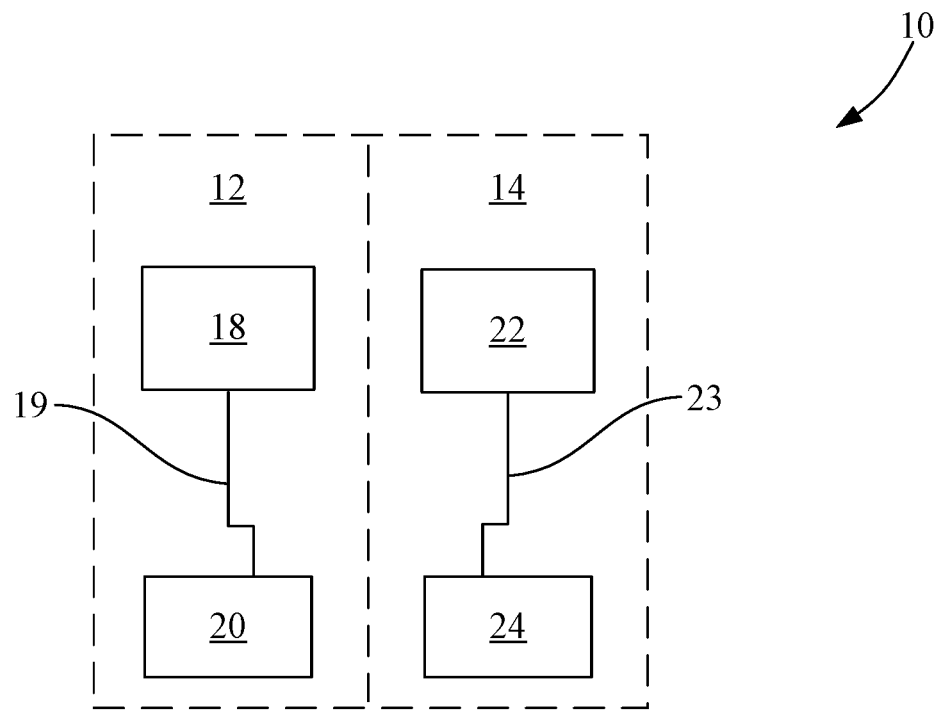
FIG. 1 is a schematic representation of a system for treating a vascular lesion in a patient, the system having a non-invasive high intensity focused ultrasound system, a non-invasive ultrasound imaging system, and a biomarker insertion device.
Figure 1:
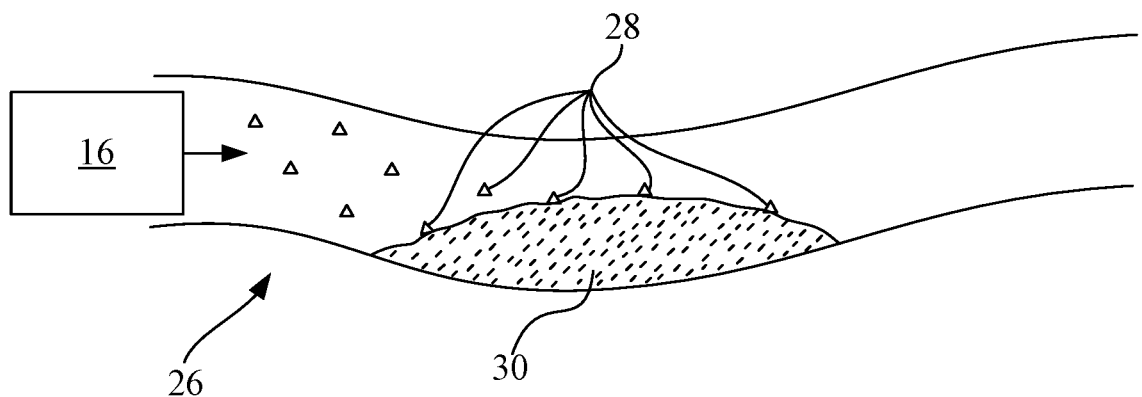

Referring now to the drawings, and more particularly to FIG. 1, there is shown a system 10 for use in treating a vascular lesion in accordance with an aspect of the invention. System 10 includes a non-invasive high intensity focused ultrasound (HIFU) system 12, a non-invasive ultrasound imaging system 14, and a biomarker insertion device 16.

Non-invasive HIFU system 12 includes a HIFU generator 18 coupled to a HIFU device 20, e.g., by a first multiconductor cable 19. In the present embodiment, HIFU device 20 is an HIFU probe. HIFU generator 18 is operable to generate a HIFU emission. HIFU device 20 receives the HIFU emission from HIFU generator 18. The frequency of the HIFU emission may be tuned at the HIFU device 20, e.g., by tuning an oscillator/crystal circuit in HIFU device 20. HIFU device 20 applies the HIFU emission with the tuned frequency to a vascular lesion 30 in a vascular region 26 to break up the vascular lesion.

HIFU device 20 is operable to tune the frequency of the HIFU emission in an exemplary range, for example, of 1 megahertz (MHz) to 5 MHz, or, more particularly, for example, in a range of 0.8 MHz to 3.2 MHz. HIFU device 20 is operable to tune the HIFU emission to any frequency in the desired exemplary range, for example, between 1 MHz to 5 MHz. Tuned frequencies of the HIFU emissions with a frequency range of approximately 1 MHz to approximately 5 MHz generate focal intensities in the range of approximately 1,000 Watts/square centimeter (W/cm²) to approximately 10,000 W/cm². As another example, HIFU device 20 is operable to tune the HIFU emission to any frequency in an exemplary range, for example, of 0.8 MHz to 3.2 MHz.

Optionally, HIFU device 20 may be operable to also tune the power of the HIFU emission in conjunction with the tuned frequency.

HIFU device 20 is operable to be tuned based on the determined lesion type. In an exemplary embodiment, at least the frequency of the HIFU emission is tuned based on the determined lesion type of the vascular lesion that has been imaged under ultrasound imaging, and optionally, the power may also be tuned.

HIFU device 20, e.g., the HIFU probe, is operable to focus the HIFU emission in an exemplary range, for example, from 9 cm to 16 cm, from HIFU device 20. HIFU device 20 focuses the HIFU emission on vascular lesion 30 with a volume as small as 10 mm³ and maintains HIFU device 20's effectiveness at breaking up vascular lesion 30.

Because the HIFU device 20 focuses on small volumes, an ablation of a larger HIFU target can be achieved by multiple sonications of the HIFU device 20 in a matrix format that can be repeated as many times as required. There are occasions when HIFU device 20 is applied in a matrix format across vascular region 26 for maximum effectiveness in ablating vascular lesion 30. The HIFU emission may be applied according to a matrix format, which refers to a plurality of arrangements of crystals in the HIFU device 20. A clinician has the option of applying the HIFU emission according to the matrix format by selecting one or more portions of a plurality of arrangements of crystals in the HIFU device 20 to be "on" or by selecting one or more portions of a plurality of arrangements of crystals in the HIFU device 20 to be "off".

In another example, HIFU device 20 is operable to break up vascular lesion 30 in short bursts of application of the HIFU emission with the tuned frequency. The short bursts of application may be, for example, 3 seconds or less. HIFU emissions, even those applied for less than 3 seconds, may results in cell destruction, protein denaturation, and coagulation necrosis.

Non-invasive ultrasound imaging system 14 includes an ultrasound console 22 coupled to an ultrasound imaging probe 24, e.g., by a second multi-conductor cable 23. Ultrasound imaging probe 24 is capable of delivering ultrasound to an object and receiving reflected ultrasound signals for the generation of a diagnostic ultrasound image. Non-invasive ultrasound imaging system 14 produces ultrasound images, for example, an image of a biomarker 28 in vascular region 26, i.e. "imaged biomarker".

In the present embodiment, non-invasive HIFU system 12 and non-invasive ultrasound imaging system 14 may be integrated so that HIFU device 20 and ultrasound imaging probe 24 are contained within the housing of a single, integrated probe, which may be handheld or for use in a stereotactic system.

System 10 of FIG. 1 also includes a biomarker insertion device 16. Biomarker insertion device 16 is designed to introduce biomarker 28 (e.g., consisting of a plurality of particles) into a vascular region 26. For example, biomarker insertion device 16 may be a syringe-type hypodermic needle for introduction of biomarker 28 into the bloodstream, wherein biomarker 28 may be carried by a fluid ejected from the needle.

In the present embodiment, biomarker 28 may be used to bind to one or more lesion types of a plurality of lesion types. Once biomarker 28 binds to the lesion type of a plurality of lesion types, biomarker 28 produces a specific image brightness for that particular lesion type under ultrasound imaging that will differ from the respective image brightnesses of other lesion types under ultrasound imaging. The plurality of lesion types may be, for example, fatty, calcified, and fibrous lesion types, and the associated image brightnesses of biomarker 28 may be, on a scale of 1 to 3 in image brightness, "1" for fatty, "2" for calcified, "3" for fibrous.

For example, once biomarker 28 binds to a particular lesion type, such as, e.g., calcified, the resulting image brightness of the imaged biomarker 28 under ultrasound imaging is "2", which the system 10 or a clinician determines is associated with the particular lesion type, in this example, calcified. For example, a biomarker composed of gold nanoparticles attaches to a calcified lesion type. Thus, an image brightness of an imaged biomarker 28, which may be displayed on the ultrasound console 22, differs based on the particular lesion type of the plurality of lesion types to which biomarker 28 binds.

In the exemplary system shown in FIG. 1, vascular lesion 30 is composed of a lesion type to which biomarker 28 is capable of binding, attaching, or tagging. In FIG. 1, biomarker 28, e.g., consisting of gold nanoparticles, is shown binding itself to vascular lesion 30. Under ultrasound imaging produced by non-invasive ultrasound imaging system 14, the imaged biomarker is observed. Then, the lesion type of vascular lesion 30 is determined.

Thereafter, in accordance with an aspect of the invention, the frequency of the HIFU emission of non-invasive HIFU system 12 is tuned based on the determined lesion type, producing a "tuned frequency" in the process. HIFU device 20 applies the HIFU emission of non-invasive HIFU system 12 at the tuned frequency to vascular region 26 to break up vascular lesion 30. The process may be repeated if other lesion types are present in vascular region 26.

Figure 2:
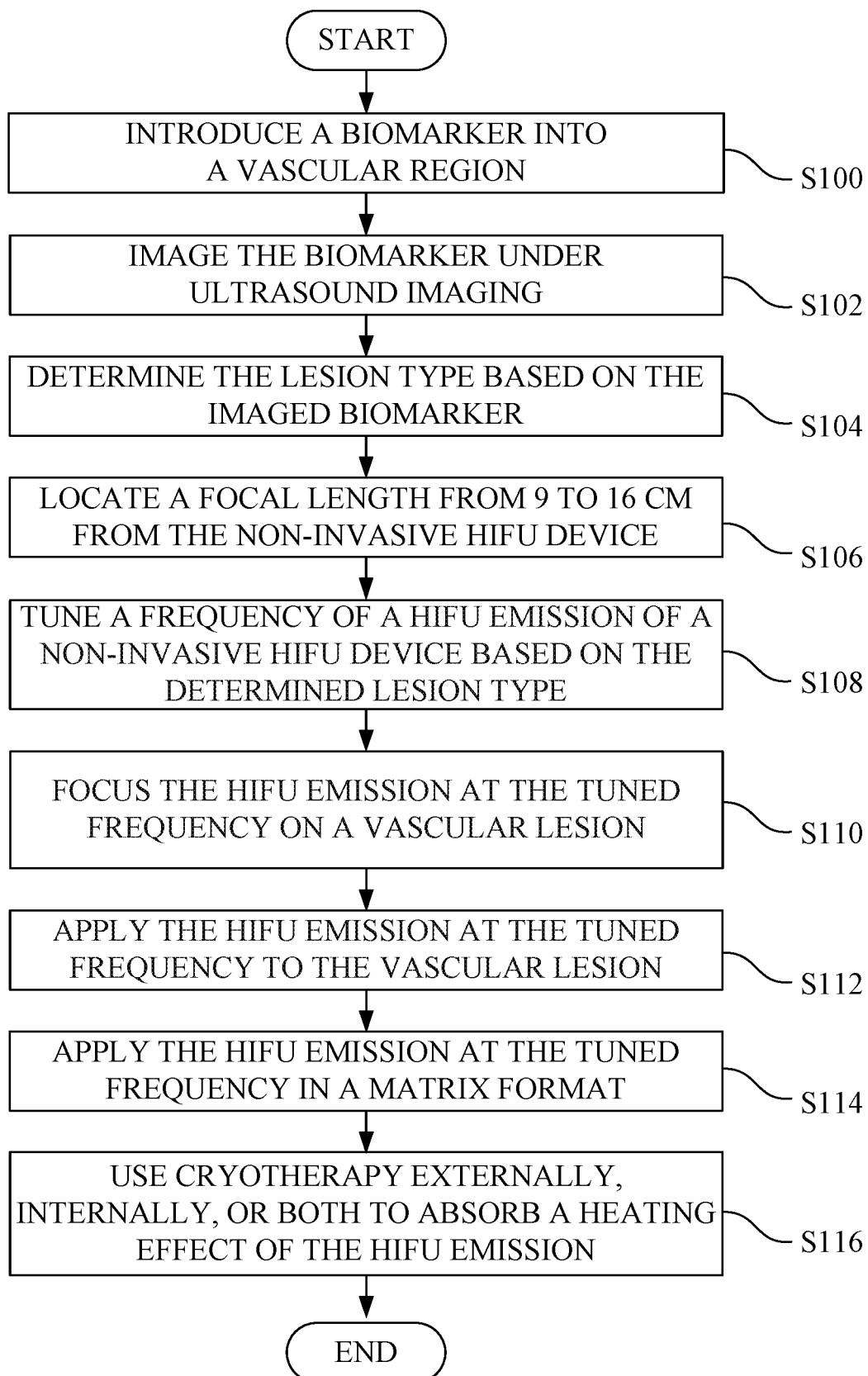
FIG. 2 is a flowchart of a method according to an aspect of the present invention.

FIG. 2 is a flowchart of an exemplary method according to an aspect of the present invention, suitable for use with system 10 depicted in FIG. 1 for treating a vascular lesion in a patient. Thus, the method of FIG. 2 will be described with reference to FIG. 1.

At step S100, with reference to FIG. 1, biomarker 28 is introduced into vascular region 26. Subsequently, biomarker 28 binds to the lesion type of vascular lesion 30. Once biomarker 28 binds with the lesion type of vascular lesion 30, biomarker 28 produces a specific image brightness for that particular lesion type under ultrasound imaging that will differ from the respective image brightnesses of other lesion types under ultrasound imaging.

At step S102, biomarker 28 is imaged under diagnostic, ultrasound imaging. Ultrasound imaging probe 24 of the non-invasive ultrasound imaging system 14 produces ultrasound that is delivered to vascular region 26. Biomarker 28 is imaged under ultrasound imaging for the purpose of determining the lesion type based on the image brightness of the imaged biomarker 28. In an exemplary embodiment, the image of the biomarker 28 bound to the vascular lesion 30 is produced on the ultrasound console 22. The imaged biomarker 28 is observable on the ultrasound console 22.

At step S104, the lesion type is determined based on the imaged brightness of the imaged biomarker 28. The result of step S104 is a determined lesion type. The determined lesion type is distinguishable from other lesion types of the plurality of lesion types. The plurality of lesion types may be, for example, fatty, calcified, and fibrous lesion types, and the associated image brightnesses of biomarker 28 may be, for example, on a scale of 1 to 3 in image brightness, "1" for fatty, "2" for calcified, "3" for fibrous.

Optionally, an exemplary method includes step S106. At step S106, a focal length is located from HIFU device 20. For example, the focal length is located from 9 cm to 16 cm from HIFU device 20. In the example, HIFU device 20 is operable to focus the HIFU emission from 9 cm to 16 cm from HIFU device 20. Thus, the application of HIFU emissions from HIFU device 20 is non-invasive to the patient.

At step S108, a frequency of a HIFU emission is tuned based on the determined lesion type from step S104. The result of step S108 is a tuned frequency.

The tuning of step S108 takes place at HIFU device 20. Each different lesion type of a plurality of lesion types has a different density or range of densities. Each lesion type is best destroyed or disintegrated at a particular tuned frequency of the HIFU emission. A tuned frequency, under which a particular lesion is optimally destroyed or disintegrated, may be one particular frequency, as may be predetermined in a lab setting. In some cases, the tuned frequency may be a particular range of frequencies under which a particular lesion is optimally destroyed or disintegrated.

The frequency of the HIFU emission may be tuned by tuning the oscillator/crystal circuit of HIFU device 20, and also may include adjusting the focal length of HIFU device 20. Alternatively, frequency specific HIFU devices may be provided and swapped out to select the desired tuned frequency.

Optionally, at step S108, another characteristic of the HIFU emission of the non-invasive HIFU device 20 also may be tuned based on the determined lesion type, resulting in a tuned characteristic. For example, the characteristic may be selected from a group of power/intensity and focal length/focal depth.

HIFU device 20 is operable to be tuned based on the determined lesion type. In an exemplary embodiment, at least the frequency of the HIFU emission is tuned based on the determined lesion type of the vascular lesion that has been imaged under diagnostic, ultrasound imaging.

According to an exemplary method, a clinician may choose to follow step S110. At step S110, the HIFU emission is focused on vascular lesion 30 having a volume as small as 10 mm$^3$. HIFU emissions can increase the tissue temperature in a focal area up to 60 degrees C. and as high as 100 degrees C. in seconds, which is sufficient to induce thermal coagulation, but is also sufficient to minimize blood perfusion effects. An advantage of focusing the HIFU emissions precisely on tissue volumes as small as 10 mm$^3$ is to minimize damaging intervening and surrounding tissue.

At step S112, the HIFU emission at the tuned frequency is applied to vascular lesion 30 to cause vascular lesion 30 to break up. For example, HIFU device 20 applies the HIFU emission with the tuned frequency on vascular lesion 30 and, as a result, vascular lesion 30 is destroyed or disintegrated. Step S112 may be repeated as many times as required to ablate the lesion.

If step S108 was followed such that a tuned frequency and a tuned power resulted, then at step S112, the HIFU emission at the tuned frequency and the tuned power is applied to vascular lesion 30 to break up vascular lesion 30.

According to an exemplary method, a clinician may choose to follow step S114. At step S114, the HIFU emission at the tuned frequency is applied in a matrix format. The matrix format is advantageous, because it allows for a tuned frequency to be applied to larger lesions. As described above in step S110, the tuned frequency of a HIFU emission can be tightly and precisely focused on small volumes, such as 10 mm$^3$, to avoid damaging intervening and surrounding tissues. Advantageously, step S114 provides for a method of treating lesions with larger volumes, such as those larger than 10 mm$^3$, by applying the HIFU emission at the tuned frequency in a matrix format, such as, for example, the selection of a grid pattern arrangement of crystals to be "on", over vascular lesion 30. Moreover, step S114 can be repeated as many times as required to ablate vascular lesion 30.

At step S116, a heating effect of the HIFU emission may be absorbed by using cryotherapy externally, internally, or both. HIFU emissions can increase the tissue temperature in a focal area up to 60 degrees C. and as high as 100 degrees C. in seconds, sufficient to induce thermal coagulation while minimizing blood perfusion effects. Cryotherapy can be applied externally, for example with ice baths, or internally, for example with irrigation, or both to minimize the effect of any thermal effects on the surrounding tissue, intervening tissue, or both that are not intended to receive the HIFU emission of HIFU device 20. In clinical practice, step S116 may be followed immediately after step S112 or concurrently with step S112, particularly when step S116 includes internal cryotherapy. Moreover, when step S116 includes external cryotherapy, the external cryotherapy is often applied to the vascular region prior to step S112.

The exemplary method of FIG. 2 may be repeated as often as necessary. For instance, the exemplary method of FIG. 2 may be repeated when there is more than one vascular lesion present in the vascular region. Additionally, the exemplary method of FIG. 2 may be repeated when more than one lesion type is present in the vascular region.

It is noted that the sequential order of the process set forth above is by example. The order of some of the process steps may be changed from the specific order set forth, or combined as a single act. For example, it is to be understood that process acts of S114 and S116 may occur simultaneously.

Figure 3:
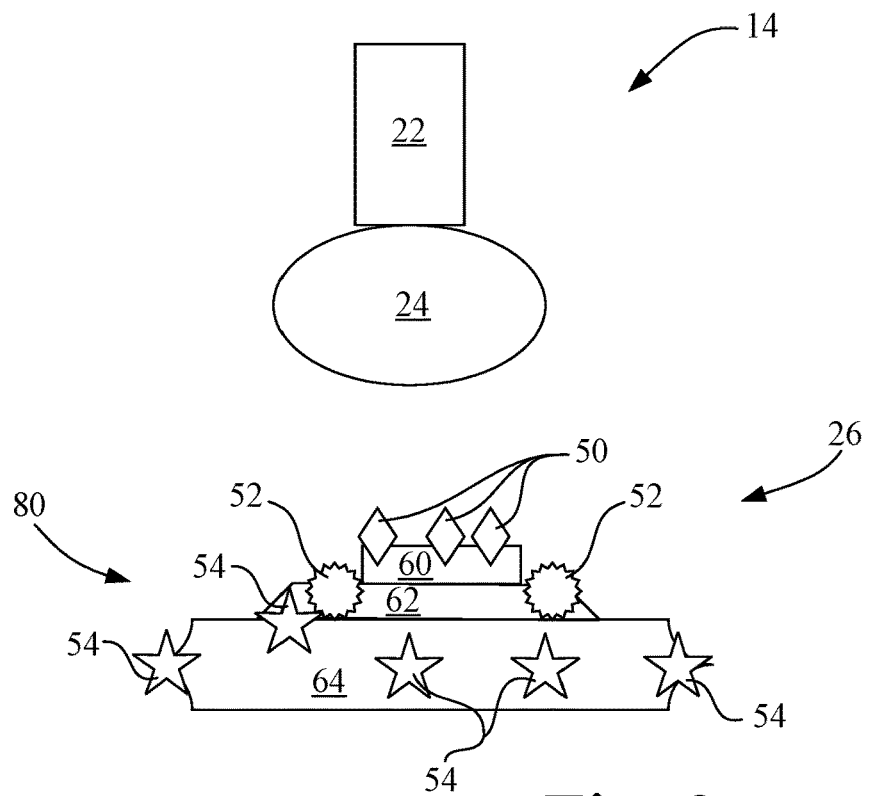
Figure 4:
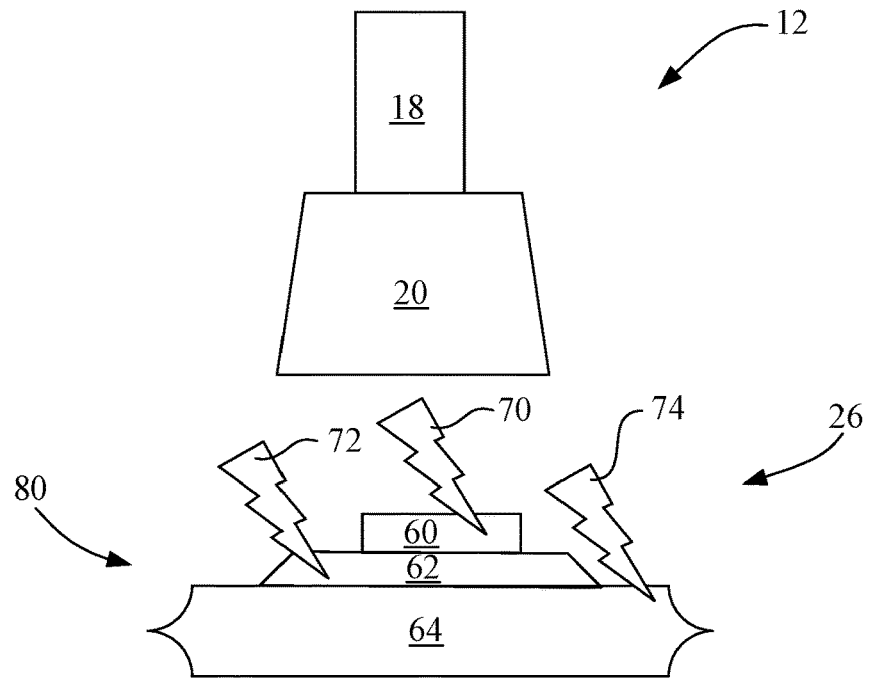

FIGS. 3 and 4 depict a second embodiment of the system for treating a vascular lesion 80 in a patient. FIG. 3 is a schematic representation of non-invasive ultrasound imaging system 14, and FIG. 4 is a schematic representation of non-invasive HIFU system 12. Vascular lesion 80 is composed of a plurality of lesion types 60, 62, 64. For example, lesion type 60 is fibrous; lesion type 62 is fatty; and lesion type 64 is calcified.

Biomarker insertion device 16 delivers biomarkers 50, 52, 54 intravenously into the vascular region 26 having vascular lesion 80. FIG. 3 shows that each of the respective biomarkers 50, 52, 54 separates as each biomarker 50, 52, 54 binds to a distinct lesion type 60, 62, 64, respectively. According to this example, biomarker 50 binds to lesion type 60, such as e.g., fibrous; biomarker 52 binds to lesion type 62, such as, e.g., fatty; and biomarker 54 binds to lesion type 64, such as, e.g., calcified. For example, biomarker 54 may be gold nanoparticles, which attach to a calcified lesion type.

Once each of the biomarkers 50, 52, 54, respectively, binds with the lesion types 60, 62, 64, respectively, the visualization of lesion types 60, 62, 64 is enhanced under diagnostic ultrasound imaging by the non-invasive ultrasound imaging system 14, as shown in FIG. 3. For example, the image brightness of biomarker 52 may be, on a scale of 1 to 3 in image brightness, "1" for fatty; the image brightness of biomarker 50 may be, on a scale of 1 to 3 in image brightness, "3" for fibrous; and the image brightness of biomarker 54 may be, on a scale of 1 to 3 in image brightness, "2" for calcified.

Once the lesion types 60, 62, 64 have been identified under diagnostic, ultrasound imaging by the non-invasive ultrasound imaging system 14 shown in FIG. 3, the non-invasive HIFU system 12 is tuned to produce a HIFU emission with a tuned frequency to specifically target the determined lesion type of interest. The frequency of the HIFU emission may be tuned, as described above. For example, tuned frequency 70 has been tuned for application to disintegrate or destroy determined lesion type 60, such, as e.g., fibrous; tuned frequency 72 has been tuned for application to disintegrate or destroy determined lesion type 62, such as, e.g., fatty; and tuned frequency 74 has been tuned for application to disintegrate or destroy determined lesion type 64, such as, e.g., calcified. On application of each tuned frequency 70, 72, 74, respectively, to each three lesion type 60, 62, 64, respectively, making up vascular lesion 80, vascular lesion 80 is broken up into very small pieces in the vascular region 26.

As used herein, words of degree are relative modifiers intended to indicate permissible variation from the characteristic so modified. Such terms are not intended to be limited to the absolute value of the characteristic which it modifies, but rather possessing more of the physical or functional characteristic than the opposite.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A non-invasive method for treatment of a vascular lesion, comprising:
    introducing a plurality of gold nanoparticles into a vascular region having a plurality of lesion types selected from the group consisting of fatty, calcified, and fibrous, wherein the plurality of gold nanoparticles separate into a plurality of fractions as the plurality of gold nanoparticles associate with each of the plurality of lesion types with different affinities, such that a first fraction of the plurality of gold nanoparticles associates with a first lesion type of the plurality of lesion types and a second fraction of the plurality of gold nanoparticles associates with a second lesion type of the plurality of lesion types,
    imaging the vascular region under diagnostic ultrasound imaging, wherein imaging produces a first image brightness and a second image brightness, wherein the first image brightness is generated from the association of the first fraction of the plurality of gold nanoparticles with the first lesion type and the second image brightness is generated from the association of the second fraction of the plurality of gold nanoparticles with the second lesion type;
    determining the first lesion type and second lesion types based on comparing the first image brightness and the second image brightness, thereby producing a first determined lesion type and a second determined lesion type;
    tuning a frequency of a high intensity focused ultrasound emission of a non-invasive high intensity focused ultrasound device based on the first and second determined lesion types, wherein as a result of the tuning of the frequency of the high intensity focused ultrasound emission is a tuned frequency; and
    applying the high intensity focused ultrasound emission of the non-invasive high intensity focused ultrasound device to the vascular lesion at the tuned frequency to break up the vascular lesion.

2. The method of claim 1, wherein the non-invasive high intensity focused ultrasound emission has a focal intensity from 1,000 to 10,000 W/cm$^2$.

3. The method of claim 1, wherein the tuned frequency of the high intensity focused ultrasound is 1 to 5 MHz.

4. The method of claim 1, wherein the tuned frequency of the high intensity focused ultrasound is 0.8 to 3.2 MHz.

5. The method of claim 1, further comprising:
    locating a focal length from 9 to 16 cm from the non-invasive high intensity focused ultrasound device.

6. The method of claim 1, further comprising:
    applying the high intensity focused ultrasound emission in a matrix format.

7. The method of claim 1, further comprising:
    focusing the high intensity focused ultrasound emission on the vascular lesion having a volume as small as 10 mm$^3$.

8. The method of claim 1, wherein the high intensity focused ultrasound emission is applied to the vascular lesion for less than 3 seconds.

9. The method of claim 1, further comprising:
    using an ice bath externally to absorb the heating effects of the high intensity focused ultrasound emission.

10. The method of claim 1, further comprising:
    irrigating a tissue proximate to the vascular lesion to absorb a heating effect of the high intensity focused ultrasound emission.

11. The method of claim 1, wherein:
    the step of tuning further comprises tuning a power of the high intensity focused ultrasound emission of the non-invasive high intensity focused ultrasound device based on the first and second determined lesion types, wherein as the result of the tuning of the power of the high intensity focused ultrasound emission is a tuned power, and
    the step of applying further comprises applying the high intensity focused ultrasound emission of the non-invasive high intensity focused ultrasound device to the vascular lesion at the tuned frequency and the tuned power to break up the vascular lesion.

12. The method of claim 11, wherein the tuned power of the non-invasive high intensity focused ultrasound emission has a focal intensity from 1,000 to 10,000 W/cm$^2$.

13. The method of claim 1, wherein:
    focusing a focal depth of the high intensity focused ultrasound emission of the non-invasive high intensity focused ultrasound device based on locations of the first and second determined lesion types relative to an ultrasound imaging probe, wherein as the result of the tuning of the focal depth of the high intensity focused ultrasound emission is a tuned focal depth, and
    the step of applying further comprises applying the high intensity focused ultrasound emission of the non-invasive high intensity focused ultrasound device to the vascular lesion at the tuned frequency and the tuned focal depth to break up the vascular lesion.

14. The method of claim 1, wherein:
    the method further comprises determining locations of the first and second determined lesion types from an ultrasound imaging probe, thereby producing a determined location of the first and second determined lesion types;

the step of tuning further comprises:
- tuning a power of the high intensity focused ultrasound emission of the non-invasive high intensity focused ultrasound device based on the determined lesion type, wherein as the result of the tuning of the power of the high intensity focused ultrasound emission is a tuned power, and
- tuning a focal depth of the high intensity focused ultrasound emission of the non-invasive high intensity focused ultrasound device based on the determined locations of the first and second determined lesion types, wherein as the result of the tuning of the focal depth of the high intensity focused ultrasound emission is a tuned focal depth; and the step of applying further comprises applying the high intensity focused ultrasound emission of the non-invasive high intensity focused ultrasound device to the vascular lesion at the tuned frequency, the tuned power, and the tuned focal depth to break up the vascular lesion.

15. The method of claim 1, wherein a third fraction of the plurality of gold nanoparticles associates with a third lesion type of the plurality of lesion types.

16. The method of claim 15, wherein imaging produces a third image brightness generated from the association of the third fraction of the plurality of gold nanoparticles with the third lesion type.

* * * * *

UNITED STATES PATENT AND TRADEMARK OFFICE
CERTIFICATE OF CORRECTION

| | | |
|---|---|---|
| PATENT NO. | : 11,497,465 B2 | |
| APPLICATION NO. | : 16/663530 | |
| DATED | : November 15, 2022 | |
| INVENTOR(S) | : Ranjani Sampath Kumaran | |

It is certified that error appears in the above-identified patent and that said Letters Patent is hereby corrected as shown below:

On the Title Page

In page 2, Column 2, item (56), other publications, cite no. 2, after "Ergün,", delete "A. Sanh" and insert --A. Sanli--, therefor.

Signed and Sealed this
Twenty-seventh Day of December, 2022

Katherine Kelly Vidal
*Director of the United States Patent and Trademark Office*